(12) United States Patent
Wedler et al.

(10) Patent No.: US 9,036,150 B2
(45) Date of Patent: May 19, 2015

(54) SCATTERED RADIATION FIRE DETECTOR AND METHOD FOR THE AUTOMATIC DETECTION OF A FIRE SITUATION

(71) Applicants: Gerd Wedler, Dresden (DE); Ralf Behrens, Herrsching (DE); Erwin Berchtold, Penzberg (DE); Markus Schulz, Stockdorf (DE); Thorsten Schultze, Ratingen (DE); Ingolf Willms, Erkrath (DE); Wolfgang Kruell, Duisburg (DE)

(72) Inventors: Gerd Wedler, Dresden (DE); Ralf Behrens, Herrsching (DE); Erwin Berchtold, Penzberg (DE); Markus Schulz, Stockdorf (DE); Thorsten Schultze, Ratingen (DE); Ingolf Willms, Erkrath (DE); Wolfgang Kruell, Duisburg (DE)

(73) Assignee: APPARATEBAU GAUTING GMBH, Gauting (DE)

( * ) Notice: Subject to any disclaimer, the term of this patent is extended or adjusted under 35 U.S.C. 154(b) by 212 days.

(21) Appl. No.: 13/684,786

(22) Filed: Nov. 26, 2012

(65) Prior Publication Data
US 2013/0135607 A1    May 30, 2013

(30) Foreign Application Priority Data

Nov. 25, 2011 (DE) .......................... 10 2011 119 431

(51) Int. Cl.
*G01N 21/53* (2006.01)
*G08B 17/107* (2006.01)
*G01N 21/47* (2006.01)

(52) U.S. Cl.
CPC ........ *G01N 21/53* (2013.01); *G01N 2021/4711* (2013.01); *G08B 17/107* (2013.01)

(58) Field of Classification Search
CPC ....... G01N 21/00; G01N 21/53; G08B 17/107
USPC .......................................................... 356/338
See application file for complete search history.

(56) References Cited

U.S. PATENT DOCUMENTS

| 6,218,950 | B1 | 4/2001 | Politze et al. | |
|---|---|---|---|---|
| 7,239,387 | B2* | 7/2007 | Politze et al. | 356/338 |
| 7,298,479 | B2* | 11/2007 | Politze et al. | 356/338 |
| 2004/0066512 | A1* | 4/2004 | Politze et al. | 356/338 |
| 2007/0229824 | A1* | 10/2007 | Politze et al. | 356/336 |

FOREIGN PATENT DOCUMENTS

| DE | 44 14 166 C1 | 12/1995 |
|---|---|---|
| DE | 698 06 404 T2 | 11/2002 |

(Continued)

OTHER PUBLICATIONS

English Abstract of GB 2330410 A, dated Apr. 21, 1999 (corresponding to DE 698 06 404 T2).

*Primary Examiner* — Roy M Punnoose
(74) *Attorney, Agent, or Firm* — Scully, Scott, Murphy & Presser, P.C.

(57) ABSTRACT

A scattered radiation fire detector having radiation sources of different wavelengths and a scattered radiation sensor, which are arranged and formed so that their optical axes are directed at a common centre of a scattering volume. A sensor unit is furthermore formed to register forward scattering $I_1(\lambda_{1,fwd})$ of a first radiation source, forward scattering $I_2(\lambda_{2,fwd})$ of a second radiation source and backward scattering $I_3(\lambda_{1,bwd})$ of a further first radiation source, to calculate scattered radiation intensity quotients $Q_1=I_1(\lambda_{1,fwd})/I_2(\lambda^{2,fwd})$, $Q_2=I_1(\lambda_{1,fwd})/I_3(\lambda_{1,bwd})$ and $Q_3=I_2(\lambda_{2,fwd})/I_3(\lambda_{1,bwd})$ and to detect the existence of a fire situation using the scattered radiation intensity quotients.

15 Claims, 2 Drawing Sheets

(56) References Cited

FOREIGN PATENT DOCUMENTS

| | | |
|---|---|---|
| DE | 10 2007 021 452 B4 | 12/2009 |
| DE | 10 2004 032 294 B4 | 2/2012 |
| EP | 1408469 A2 | 4/2004 |
| EP | 1884904 A1 | 2/2008 |
| WO | WO0007161 A1 | 2/2000 |

* cited by examiner

SCATTERED RADIATION FIRE DETECTOR AND METHOD FOR THE AUTOMATIC DETECTION OF A FIRE SITUATION

BACKGROUND OF THE INVENTION

The invention relates to a scattered radiation fire detector and to a method for the automatic detection of a fire situation.

DISCUSSION OF THE PRIOR ART

Scattered radiation tire detectors and methods for the automatic detection of a fire situation are known in a very wide variety of configurations and variants. For example, reference is made to U.S. Pat. No. 6,218,950 B1, EP 1 408 469 B1, DE 44 14 166 C1 and DE 10 2007 021 452 B4.

An essential aspect in the case of scattered radiation fire detectors relates to the accuracy or sensitivity of the detection of a fire situation. Specifically, what is important is to minimize error rates, whether actual fire situations not being detected as such or an alarm erroneously being triggered even though a fire situation does not actually exist. In order to increase the sensitivity, for scattered radiation fire detectors, particularly in the cited documents, it has been proposed inter alia to use different wavelengths, forward and/or backward scattering and/or ratios or differences of scattered radiation intensities. Despite the known solution approaches, there is still a need to improve the sensitivity and accuracy for the detection of a fire situation by scattered radiation fire detectors.

On the basis of this, it is an object of the invention to provide a scattered radiation fire detector having improved sensitivity and accuracy for the detection of a fire situation. Furthermore, with the same criteria, a method for detecting a fire situation is intended to be provided.

SUMMARY OF THE INVENTION

According to the present invention, a scattered radiation fire detector is provided which comprises two first radiation sources of a first wavelength and a second radiation source, i.e. in particular precisely one second radiation source, of a longer second wavelength.

The radiation sources are formed in order to emit radiation, which in the context of the invention preferably lies in the visible spectral range or in the infrared spectral range. The first radiation sources, which may particularly preferably emit in the visible spectral range, may in principle be any light sources, but particularly preferably light-emitting diodes (LEDs) with emission in the visible spectral range. The second radiation source, which preferably emits in the infrared (IR) spectral range, is preferably an LED having emission in the IR spectral range.

The scattered radiation fire detector furthermore comprises a sensor unit, i.e. in particular precisely one sensor unit, having a single scattered radiation sensor or individual scattered radiation sensors sensitive to the first and second wavelengths. As a radiation-sensitive element, the sensor unit preferably comprises a reception diode which, according to the comments above, is sensitive both to the first wavelength, i.e. in the visible spectral range, and to the second wavelength, i.e. in the IR spectral range.

In this case, the term "sensitive" is intended in particular to mean that the sensor unit, in particular the reception diode, can detect radiation of a corresponding wavelength with a sensitivity which is suitable and sufficient for a scattered radiation fire detector.

The scattered radiation sensor is formed in order to register scattered radiation. Scattered radiation occurs in the scattered radiation fire detector for example owing to the radiation of the first and/or second wavelength being shone onto a given, i.e. defined scattering volume and scattered by particles, in particular solid and/or liquid particles, or aerosols, located in the scattering volume.

According to the proposed scattered radiation fire detector, the first radiation sources, the second radiation source and the scattered radiation sensor are arranged and formed in such a way that their optical axes are directed at a common centre of a scattering volume. In particular, the first radiation sources, the second radiation source and the scattered radiation sensor are arranged in such a way that the principal emission axes of the radiation sources and the principal incidence axis of the scattered radiation sensor intersect at the centre. The principal emission axes or the corresponding principal emission directions, and the principal incidence axis and the corresponding principal incidence direction, are defined by the respective emission cones and incidence cone which, as will be described in more detail below, may be adjusted by masks.

Furthermore, the first radiation sources, the second radiation source and the scattered radiation sensor are arranged and formed in such a way that i. forward scattered radiation intensities $I_1(\lambda_{1,fwd})$ of one of the first radiation sources, ii. forward scattered radiation intensities $I_2(\lambda_{2,fwd})$ of the second radiation source and iii. backward scattered radiation intensities $I_3(\lambda_{1,bwd})$ of the other of the first radiation sources can be detected by the scattered radiation sensor, or the sensor unit.

Here, $I_x$ with x=1, 2, 3 denotes the respective scattered radiation intensities, with the respective wavelength, i.e. the first wavelength $\lambda_1$ or the second wavelength $\lambda_2$, and the respective scattering direction "fwd" for forward scattering or "bwd" for backward scattering being indicated in brackets.

The sensor unit of the scattered radiation fire detector is adapted and formed in order to calculate the scattered radiation intensity quotients $Q_1=I_1(\lambda_{1,fwd})/I_2(\lambda_{2,fwd})$, $Q_2=I_1(\lambda_{1,fwd})/I_3(\lambda_{1,bwd})$ and $Q_3=I_2(\lambda_{2,fwd})/I_3(\lambda_{1,bwd})$ and in order to use them for the decision regarding the existence of a fire situation.

The proposed scattered radiation fire detector has a comparatively simple structure and can be produced with comparatively few components. Moreover, precisely by taking into account the indicated scattered radiation intensities and the indicated quotients, it is possible to achieve a comparatively high sensitivity and accuracy. In particular, a particularly advantageous, i.e. low, false alarm rate can be achieved.

The particularly high sensitivity together with high accuracy, and concomitantly comparatively low false alarm rate, can be achieved in particular when the scattered radiation fire detector is operated as follows:

A decision regarding the existence of a fire situation or the nonexistence of a fire situation is made exclusively with the aid of the forward scattered radiation of the second wavelength, i.e. a signal determined or obtained from the forward scattered radiation of the second wavelength, in particular the forward scattered radiation intensity $I_2(\lambda_{2,fwd})$ or a quantity derived or determined therefrom.

To this end, the value range envisaged for the signal is divided into one or more ranges representative of fire situations and into one or more ranges representative of non-fire situations. If the signal lies in a range representative of fire situations, then the scattered radiation fire detector, for example with the aid of a microelectronic circuit or the like, may output a corresponding alarm signal which may be delivered outwards for example in acoustic and/or visual form and/or forwarded to a central fire detection station.

Specifically, the signal may be compared, in particular continuously or with a certain clock cycle, with one or more threshold values, and the alarm signal may be output if the threshold value is exceeded into a range representative of a fire event. If the signal lies in a range representative of a non-fire situation, then correspondingly no alarm signal is output and/or a previously output alarm signal or alarm status is cancelled.

In a simple case, a corresponding decision matrix is such that the existence of a non-fire situation is inferred below or above the threshold value, and the existence of a fire situation is inferred above or below the threshold value, respectively.

In the specific exemplary mode of operation described here, the determined or calculated scattered radiation intensity quotients and/or combinations thereof are employed in order to modify the threshold value, or optionally the threshold values. For example, it is possible for the threshold value or values to be raised or lowered if one or more of the scattered radiation intensity quotients lie in a respectively predetermined value range between two limit values and/or the respective limit values are fallen below and/or exceeded. So to speak, a comparison of the scattered radiation intensity quotients with limit values or value ranges predetermined in a fixed fashion is carried out.

The scattered radiation intensity quotients used and specifically proposed according to the invention permit a comparatively accurate classification of respectively existing scattering conditions and scattering ratios, in particular classification of the particles or aerosols in the scattering volume which lead to increased scattered radiation.

The basis of the proposed scattered radiation fire detector is now that in the event of a fire, particles or aerosols, such as soot, suspended particles and the like are generated which, if the scattered radiation smoke detector is installed suitably, enter the scattered volume and lead to an increase in the forward scattered radiation intensity $I_2(\lambda_{2,fwd})$ of the second radiation source.

However, particles or aerosols which are not generated by fire, burning and the like, for example dust and other suspended particles, also increase the scattered radiation intensity and in the absence of further measures, with sole use of the forward scattering of a single wavelength, such as the second wavelength in this case, would lead to categorization as a fire situation. This would entail a comparatively high error rate. It is therefore necessary to identify the particles not caused by fire or burning, or the corresponding scattering conditions, and classify them as a non-fire situation.

As is known, the scattered radiation intensity depends on the wavelength respectively used, the size of the particles or aerosols and on the scattering angle. Through the use of the scattered radiation intensity quotients proposed according to the invention, which take into account special forward and backward scattered radiation intensities for the first and second wavelengths, it is possible to achieve a comparatively accurate classification or discrimination of particles or aerosols in terms of whether they are caused by fire or burning or other sources of a different type.

If there are particles or aerosols in the scattering volume which can be classified with the aid of the scattered radiation intensity quotients as not caused by fire, burning etc., then for example the threshold value for the forward scattered radiation intensity $I_2(\lambda_{2,fwd})$ may be modified, for example raised, in such a way that the forward scattered radiation intensity for the second wavelength, which is thereupon used for the detection of a fire situation, lies in a range representative of a non-fire situation, for example below the threshold value. If further aerosols caused by fire or burning, such as soot, additionally occur in this situation, then the proportion of the scattered radiation is further increased and finally leads to the threshold value being exceeded and therefore the fire situation being detected.

By adaptation of the threshold value, the sensitivity or the responsivity of the scattered radiation fire detector can, in particular, be modified in such a way that the false alarm rate caused by particles or aerosols with an origin other than fire or burning can be significantly reduced. Examples which may be mentioned for aerosols which are not caused by fire, burning and comparable situations, and which are correctly classified by the scattered radiation fire sensory according to the invention, at least with a comparatively high reliability, are: dust particles, substances dispersed in air from sprays, in particular deodorants, and the like, cigarette smoke, etc.

According to a particularly preferred configuration, the first wavelength lies between 460 nm and 540 nm, preferably at about 525 nm i.e. in the green spectral range, or at about 470 nm i.e. in the blue spectral range. Preferably, the second wavelength in this configuration lies in the infrared spectral range, in particular between 890 nm and 990 nm, preferably at about 940 nm. The wavelength ranges indicated have proven particularly advantageous for the scattered radiation intensity quotients used in the scattered radiation fire detector according to the invention. The wavelengths mentioned are advantageous in particular for the specific detection of fire situations and non-fire situations, particularly for the classification of particles or aerosols which are not caused by fire or burning.

According to another advantageous configuration of the invention, the first radiation sources, the second radiation source and the scattered radiation sensor are arranged essentially on a circle around the common centre. With such a configuration, it is possible to achieve a structure which is particularly compact and advantageous for the circulation of ambient air through the scattering volume. Furthermore, a particularly large scattering volume can be obtained in relation to the total height of the scattered radiation fire detector.

In a particularly advantageous configuration, the scattered radiation sensor is arranged at a forward scattering angle of about 60 degrees and at a backward scattering angle of about 120 degrees, in each case with respect to the principal emission directions. For forward radiation, this means that radiation emitted by a respective radiation source in a primary emission direction must be deviated, i.e. scattered, through an angle of 60 degrees in order to strike the scattered radiation sensor in the principal incidence direction. A similar consideration applies for the backward radiation, i.e. that radiation emitted by a respective radiation source in a primary emission direction must be deviated through an angle of 120 degrees in order to strike the scattered radiation sensor in the principal incidence direction.

The values indicated for forward and backward scattering have proven particularly advantageous in particular for the proposed wavelength ranges, as well as for the scattered radiation intensity quotients used.

According to another configuration of the scattered radiation fire detector, the radiation sources are respectively arranged in first housings. The housings may in particular be used to reduce the emission cone of the radiation sources of the scattered radiation sensor to a desired range. In particular, it is possible to adapt or adjust the size, in particular the diameter, of the scattering volume.

Preferably, the scattered radiation fire detector has a base body, on or with which the first housing is formed integrally. In this case, comparatively simple and economical production of the base body together with the housing is possible by the injection moulding method. As an alternative, it is also possible for the housings, or individual housings, to be formed on a cover of the scattered radiation fire detector, which can be fitted onto the base body.

For the housings, in particular for the defined restriction of the emission cones, it has proven advantageous for a plurality of fan masks, directed in a barb shape away from the exit opening and transversely to the respective optical axis, to be arranged offset behind one another between a radiation source and an exit opening of a respective first housing. Preferably, fan masks are arranged on both sides of the optical axis, i.e. the principal emission direction, of the respective radiation source, and preferably in a symmetrical position relative to the optical axis.

Similarly as in the case of the radiation sources, the scattered radiation sensor may also be arranged in a second housing, preferably formed integrally with the base body. In a similar configuration as for the first housing, a plurality of fan masks, directed in a barb shape towards the entry opening and transversely to the optical axis of the scattered radiation sensor may be arranged between the scattered radiation sensor and an entry opening of the second housing, preferably on both sides of the optical axis of the scattered radiation sensor, and preferably in a symmetrical position relative to the optical axis.

Besides the housings, corresponding masks may generally be provided in a respectively suitable arrangement in order to restrict the emission cones or the reception cone.

In order to simplify assembly of the scattered radiation fire detector, the first and second housings may have specially formed sockets and holders, into which the radiation sources or the scattered radiation sensor can respectively be inserted or engaged.

As regards the scattered radiation fire detector, it is therefore clear that an improved sensitivity and accuracy together with a comparatively simple structure can be achieved with the structure proposed according to the invention and the proposed configuration.

According to another configuration, the scattered radiation fire detector furthermore comprises at least one heating element. The heating element may be a component of a heating device of the scattered radiation fire detector. Besides the at least one heating element, the heating device may also have a controller for controlling the heating element, and possibly also an associated temperature sensor.

The heating element is adapted and formed in order to heat at least the scattering volume of the scattered radiation fire detector. The reason and purpose for a heating element is to prevent condensation mist occurring in moisture condensation situations. Condensation mist would or could lead to an increase in the scattered radiation, and therefore to erroneous triggering of the scattered radiation fire detector. By heating at least the scattering chamber, the condensation mist can be avoided so that the false alarm rate can be kept low.

The heating element may, for example, be arranged in the scattering chamber itself. Preferably, however, the heating element is installed outside the scattering chamber. According to a preferred embodiment, it is proposed that the at least one heating element should be arranged on a side, facing away from the scattering volume, of a wall which is adjacent to the scattering volume and at least partially bounds the scattering volume.

This wall may, for example, be the bottom of the base body, which may be a component of a casing of the scattered radiation fire detector. More preferably, the at least one heating element is installed directly on an electronic circuit board on which additional electronic components, for example for preprocessing, processing and postprocessing of the measurement signals of the scattered radiation measurement etc., may furthermore be arranged. Arranging the at least one heating element on a circuit board, in particular one equipped with further electronic components, has the further advantage that not only the scattering chamber but also the electronic components are heated and therefore precipitation, for example of water of condensation and the like can, at least substantially be avoided.

The aforementioned associated temperature sensor is not absolutely necessary, but it makes it possible to check the temperature, at least in the scattering chamber. The temperature measured with the aid of the associated temperature sensor may be used in order to adjust, control or regulate the operation, in particular the heating power, of the at least one heating element. The associated temperature sensor may be one of the temperature sensors already mentioned above, which may if required be used or provided for classification of the scattering behaviour.

The present invention is further directed to a method for the automatic detection of a fire situation. In this context, automatic is intended in particular to mean that the individual steps of the method are controlled or carried out by a microcontroller or an electronic circuit.

The method may be implemented in a scattered radiation fire detector according to the invention as described above, including all arrangements and configurations thereof. The method comprises the following steps:

delivering radiation of a first wavelength into a scattering volume and measuring, or determining, a first scattered radiation intensity $I_1(\lambda_{1,fwd})$ of the first wavelength generated by forward scattering in the scattering volume;

delivering radiation of a second wavelength into the scattering volume and measuring, or determining, a second scattered radiation intensity $I_2(\lambda_{2,fwd})$ of the second wavelength generated by forward scattering in the scattering volume;

delivering radiation of the first wavelength into the scattering volume and measuring, or determining, a third scattered radiation intensity $I_3(\lambda_{1,bwd})$ of the first wavelength generated by backward scattering in the scattering volume.

The steps mentioned above may also be carried out in an order other than that indicated, and individually or in groups, as well as repeatedly, i.e. successively one after the other. In the case of repeated conduct of the method, it is not absolutely necessary for the aforementioned steps respectively to be carried out equally often. The delivery of the radiation is preferably carried out in a pulsed fashion for the first and second wavelengths.

After measurement or determination of the first to third scattered radiation intensities, in a further step the first to third scattered radiation intensity quotients $Q_1$, $Q_2$ and $Q_3$ mentioned below are calculated therefrom:

$$Q_1 = I_1(\lambda_{1,fwd})/I_2(\lambda_{2,fwd}), \qquad \text{i.}$$

$$Q_2 = I_1(\lambda_{1,fwd})/I_3(\lambda_{1,bwd}), \text{ and} \qquad \text{ii.}$$

$$Q_3 = I_2(\lambda_{2,fwd})/I_3(\lambda_{1,bwd}). \qquad \text{iii.}$$

With the aid of at least one and/or a combination of several of the scattered radiation intensity quotients, more precisely as a function of the values determined or calculated therefor, classification of the scattering behaviour in the scattering volume is carried out. Classification is intended in particular to mean categorization or preliminary categorization of the scattering behaviour. This categorization or preliminary categorization may, for example, consist in varying one or more threshold values with which the forward scattered radiation intensity of the second wavelength is compared during the decision regarding the existence of a fire situation.

If individual scattered radiation intensity quotients, or combinations of scattered radiation intensity quotients reveal scattering behaviours which can comparatively reliably be associated with a non-fire situation, then for example the threshold value may be raised accordingly so that the forward scattered radiation intensity of the second wavelength lies below it and a decision that a fire situation exists is avoided. Overall this leads to a reduced sensitivity which, however, takes into account the scattering behaviour of particles or aerosols not caused by fire or burning.

If however, individual scattered radiation intensity quotients, or combinations of scattered radiation intensity quotients reveal scattering behaviours which imply a fire situation, then the threshold value may be lowered accordingly so that, with a correspondingly high forward scattered radiation intensity of the second wavelength a decision is made that a fire situation exists. Overall, this leads to an increased sensitivity.

The categorization of the various scattering behaviours into a fire situation or non-fire situation may, for example, be carried out by comparing the respectively calculated scattered radiation intensity quotients with previously established limit values or ranges. The limit values and/or ranges may, for example, be obtained by empirical measurements. With the scattered radiation intensity quotients proposed according to the invention, it is possible in particular to satisfy the requirements in force in the aviation industry for the detection of fire or burning.

In other regards, reference is made to the comments regarding the scattered radiation fire detector, which apply here mutatis mutandis.

As regards the forward and backward scattering angles and the first and second wavelengths, reference is made to the description above. In particular, the forward scattering angle may be about 60 degrees and the backward scattering angle may be about 120 degrees, in each case with respect to the principal emission directions. Furthermore, the first wavelength may lie between 460 and 540 nm, preferably at about 525 nm or at about 470 nm, and the second wavelength may lie in the infrared spectral range, in particular between 890 nm and 990 nm, preferably at about 940 nm.

Concerning further advantages of the proposed method, reference is made to the comments above and below.

In order to increase the accuracy of the scattered radiation sensor, or the method, a temperature sensor may additionally be provided. Measurement values of the temperature sensor may, for example, be used in order to increase or raise the accuracy of the classification of scattering behaviour.

It is furthermore possible for a gas sensor additionally to be provided or used, with which for example hazardous substances can be detected.

According to another method variant the scattering volume may be heated by means of a heating element at least while scattered light measurements are being carried out, i.e. during operation of the scattered light fire detector. By heating at least the scattered light volume, as already mentioned above, it is possible to avoid condensation mist formations possibly occurring in moisture condensation situations.

Heating of the scattering volume may in this case be carried out continuously, which is intended to mean that the heating element constantly emits heating power when the scattered light fire detector is in operation.

The heating may however also be carried out selectively, which is intended to mean that the heating element is only in operation when moisture condensation situations are likely or to be expected.

The latter, i.e. the occurrence of moisture condensation situations or the likelihood of the occurrence of moisture condensation situations may, inter alia, be monitored for example with the aid of temperature sensors and other sensors.

If a moisture condensation situation exists, or if one is likely, then the heating element may be activated, in particular as a precautionary measure, so that the scattering volume is heated and condensation mist formation, and as a consequence thereof the triggering of a false alarm, can at least substantially be avoided.

BRIEF DESCRIPTION OF THE DRAWINGS

Exemplary embodiments of the invention will be explained in more detail below with the aid of the figures, in which.

DETAILED DESCRIPTION OF THE INVENTION

Figure 1:
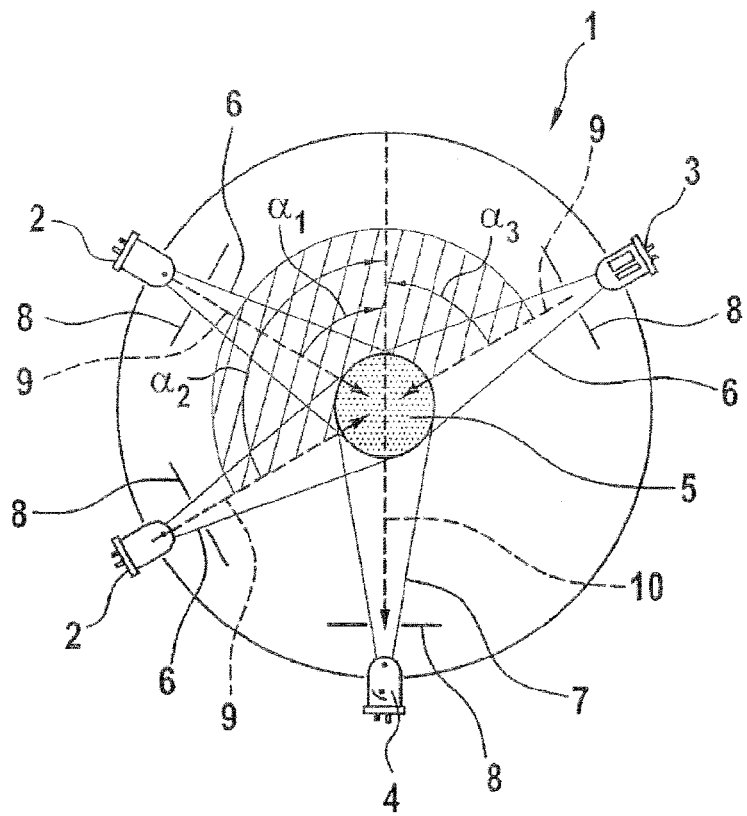
FIG. 1 schematically shows a structure of a possible embodiment of a scattered radiation fire detector according to the invention.

FIG. 1 schematically shows a structure of a possible embodiment of a scattered radiation fire detector 1 according to the invention. The scattered radiation fire detector 1 comprises two first radiation sources 2 and a second radiation source 3, as well as a scattered radiation sensor 4.

The first radiation sources 2 in the present case are light-emitting diodes (LEDs) of a first wavelength. This first wavelength preferably lies in the green or blue spectral range.

The second radiation source 3 is likewise an LED, but of a second wavelength different from the first wavelength. The second wavelength is longer than the first wavelength and lies in the infrared spectral range (IR spectral range).

The scattered radiation sensor 4 in the present case is a reception diode which is sensitive at least to radiation of the first wavelength and of the second wavelength.

The first radiation sources 2, the second radiation source 3 and the scattered radiation sensor 4 are arranged essentially on a circle. The centre of the circle coincides substantially with the centre of a measurement or scattering volume 5.

The measurement or scattering volume 5, referred to below as the scattering volume 5 for brevity, is essentially defined by emission cones 6 of the first 2 and second radiation sources 3 and by the reception cone 7 of the scattered radiation sensor 4. The emission cones 6 and the reception cone 7 are respectively represented by the outermost marginal rays in FIG. 1.

The emission cones 6 and the reception cone 7 essentially result from the aperture angle for the emission or reception of radiation in the first radiation sources 2, the second radiation source 3 and the scattered radiation sensor 3 being restricted by masks 8. The masks 8 are represented merely schematically in FIG. 1 and may be configured completely differently, in particular more elaborately. Since the case in point relates to a scattered radiation fire sensor 1, the masks should in any event be arranged and formed in such a way that radiation from the first 2 and second radiation sources 3 cannot strike the scattered radiation sensor 4 directly and/or via reflections. Besides direct incidence, at least the first reflection of the radiation from the respective radiation source onto the scattered radiation sensor 4 should also be avoided.

The emission cones 6 in the example shown are symmetrical relative to the respective principal emission direction 9 of the first radiation sources 2 and of the second radiation source 3, and in the present case collinear with the respective optical axes. The reception cone 7 is symmetrical with respect to the principal incidence direction 10 of the scattered radiation sensor 4, and in the present case collinear with the optical axis thereof.

One of the first radiation sources 2 is arranged on the circle in such a way that radiation emitted in the principal emission direction 9 can be registered by the scattered radiation sensor 4 at a forward scattering angle $\alpha_1$ of 60 degrees.

The scattering angle is meant to be the angle through which the respective vector of the principal emission direction 9 has to be rotated so that the vector is parallel to and collinear with the vector of the principal incidence direction 10.

The other of the first radiation sources 2 is arranged on the circle in such a way that radiation emitted in the principal emission direction 9 can be registered by the scattered radiation sensor 4 at a backward scattering angle $\alpha_2$ of 120 degrees.

Merely for completeness, it should be mentioned that in the context of this application scattering angles of up to 90 degrees give forward scattering and scattering angles larger than this give backward scattering.

The second radiation source 3 is arranged on the circle in such a way that radiation emitted in the principal emission direction 9 can be registered by the scattered radiation sensor 4 at a forward scattering angle $\alpha_3$ of 60 degrees.

Figure 2:
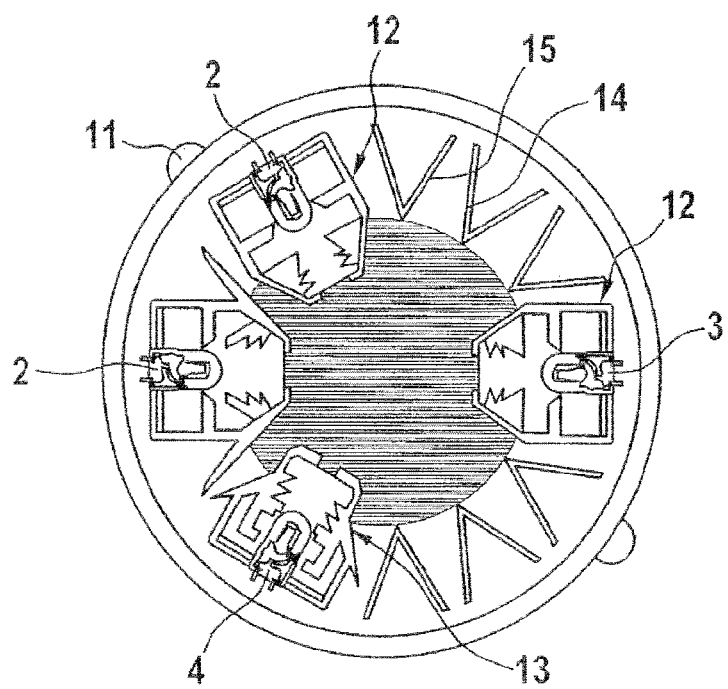
FIG. 2 shows a plan view of a base body of a scattered radiation fire detector according to FIG. 1.

FIG. 2 shows a plan view of a base body 11 of the scattered radiation fire detector 1. In particular, the first radiation sources 2, the second radiation source 3 and the scattered radiation sensor 4 are accommodated in or on the base body 11. Those elements of the base body 11 which can be seen in FIG. 2 in plan view, and respectively the upwardly facing side of the base body, are covered with a cover (not shown) in the fully assembled state. It is to be pointed out that one or more of the components and elements described with reference to FIG. 2 may also be installed on the cover.

In the example shown in FIG. 2, the two first radiation sources 2 and the second radiation source 3 are respectively mounted in a first housing 12 formed integrally with the base body 11. Here, it should be mentioned that the base body 11 may for example be produced by injection moulding. The scattered radiation sensor 4 is mounted in a second housing 13.

The first housings 12 and the second housing 13 are used on the one hand for holding and mounting, including the fastening of the first 2 and second radiation sources 3 on the base body 11, particularly in a predetermined orientation and position. On the other hand, exit openings and entry openings, respectively, are used to delimit the aperture angles of the respective emission and reception cones.

In order to obtain comparatively sharply delimited emission and reception cones, the first housings 12 and the second housing 13 have masks 8 between the respective radiation source 2 or 3 and an exit opening, and respectively between the entry opening and the scattered radiation sensor 4, as already indicated in connection with FIG. 1.

The masks 8 are in this case formed integrally with the housings and in the form of fan masks, i.e. as masks having a plurality of mask ribs arranged successively in the direction of the principal emission direction 9 and the principal incidence direction 10, respectively. The mask ribs are arranged symmetrically on both sides of the respective principal emission direction 9 or principal incidence direction 10, and in the present case are oriented in the manner of barbs towards the respective principal emission direction 9 or principal incidence direction 10.

Further masks 14 are arranged in the circumferential direction on the base body 11, each further mask 14 having at least one branch 15 extending outwards. The branches 14 are for the most part arranged in such a way, and extend in the direction from the scattering centre outwards in such a way, that a gap tapering outwards is formed between neighbouring branches, which allows ambient air to enter into the scattering centre. The further masks 14 are provided in order to at least substantially prevent ambient light from entering into the measurement or scattering volume. The further masks 14 in the configuration shown have proven to be particularly effective insofar as sufficient circulation of ambient air through the scattering volume can thereby be achieved, and at the same time the scattering volume can be shielded to a sufficient extent against ambient light.

The scattered radiation fire detector 1 described with reference to FIG. 1 and FIG. 2 furthermore has a sensor unit, of which in particular the scattered radiation sensor 4 forms a part. The sensor unit furthermore has one or more electronic controllers or circuits, in particular microcontrollers and/or microprocessors and the like, with which in particular the first radiation sources 2, the second radiation source 3 and the scattered radiation sensor 4 are controlled during operation of the scattered radiation sensor 1. The sensor unit is preferably accommodated on or in the base body 11.

The sensor unit, and in particular the first radiation sources 2, the second radiation source 3 and the scattered radiation sensor 4, are formed and in particular connected, or coupled, to the control unit or units in such a way that the scattered radiation fire detector can be operated according to the method described below.

The scattered radiation sensor 4 is formed in such a way that forward scattered radiation intensities $I_1(\lambda_{1,\mathit{fwd}})$ of one of the first radiation sources 2, forward scattered radiation intensities $I_2(\lambda_{2,\mathit{fwd}})$ of the second radiation source 3 and backward scattered radiation intensities $I_3(\lambda_{1,\mathit{bwd}})$ of the other of the first radiation sources 2 can be registered by it. To this end, the in total three radiation sources, i.e. the two first radiation sources 2 and the second radiation source 3, are operated, or powered, in a pulsed fashion and successively after one another so that scattered radiation, or more precisely scattered radiation intensities, of the one first radiation source 2, the other first radiation source 2 and the second radiation source 3 can be registered separately from one another. The order of the pulsed operation of the radiation sources is essentially arbitrary.

For the scattered radiation intensities, $\lambda$ denotes wavelength, fwd denotes forward scattering and bwd denotes backward scattering.

The decision regarding the existence of a fire situation is made with the aid of the forward scattered radiation intensities $I_2(\lambda_{2,\mathit{fwd}})$ by comparison of the intensity determined with a temporary threshold value. If $I_2(\lambda_{2,\mathit{fwd}})$ exceeds the threshold value, then a fire situation exists and the controller may output a corresponding alarm signal or the like. In this context, temporary is intended to mean that the threshold value can be modified during operation, in particular modified continuously.

In order to increase the accuracy and reliability of the scattered radiation fire detector 1, the sensor unit, in particular the controller, is furthermore configured and formed in order to adapt the threshold value continuously to the scattering behaviour respectively prevailing in the scattering volume.

The continuous adaptation of the threshold value is carried out with the aid of the following scattered radiation intensity quotients:

$$Q_1 = I_1(\lambda_{1,fwd})/I_2(\lambda_{2,fwd});\qquad\text{i.}$$

$$Q_2 = I_1(\lambda_{1,fwd})/I_3(\lambda_{1,bwd}),\text{ and}\qquad\text{ii.}$$

$$Q_3 = I_2(\lambda_{2,fwd})/I_3(\lambda_{1,bwd}),\qquad\text{iii.}$$

which are calculated by the controller from the continuously determined scattered radiation intensities $I_1(\lambda_{1,fwd})$, $I_2(\lambda_{2,fwd})$ and $I_3(\lambda_{1,bwd})$.

Without restriction of generality, for each of the scattered radiation intensity quotients, one or more value ranges are established, with the aid of which a classification of the scattering behaviour respectively existing temporarily can be carried out. The value range or ranges may be determined or found with the aid of empirical tests. It has been found that precisely the scattered radiation intensity quotients indicated are particularly suitable for carrying out a classification of the scattering behaviour with respect to the existence or nonexistence of a fire situation.

If one or more of the scattered radiation intensity quotients determined lie in a value range which is not representative of the existence of a fire situation, then the threshold value may be raised so that the scattered radiation intensity of the second radiation source 3, which is used for the final decision, does not exceed the threshold value and no alarm is triggered.

Raising of the threshold value, for example to a value $S_2$, may for example be carried out in situations in which particles or aerosols, which lead to increased scattered radiation but are not attributable to fire or burning, enter or have entered into the scattering volume, and a correspondingly increased scattered radiation behaviour is classified as a non-fire situation with the aid of the scattered radiation intensity quotients. In short, the scattering behaviour of the particles or aerosols is classified as a non-fire situation with the aid of the scattered radiation intensity quotients. The threshold value will be set in such a way that the forward scattered radiation intensity $I_2(\lambda_{2,fwd})$ of the second radiation source lies below the threshold value. In this way, erroneous triggering can reliably be avoided here for the case described.

If the scattering behaviour changes, for example because there are no (longer) particles or aerosols which are not attributable to fire or burning in the scattering volume, then the threshold value may be lowered back to an original value $S_1$, so that the original sensitivity is restored.

As particles which, on the basis of $I_2(\lambda_{2,fwd})$, could erroneously lead to the decision that a fire situation exists, dust particles, deodorant and the like may for example be envisaged.

If particles or aerosols which are caused by fire or burning enter into the scattering volume, the scattered radiation increases accordingly. The particles or aerosols attributable to fire or burning, or more precisely the corresponding scattering behaviour, will be classified accordingly by the scattered radiation intensity quotients, i.e. associated with a fire or burning situation. In particular owing to additional scattering by the particles or aerosols attributable to fire or burning, the forward scattered radiation intensity $I_2(\lambda_{2,fwd})$ of the second radiation source lies or rises above the threshold value $S_1$ or $S_2$, which is detected by the scattered radiation fire detector as a fire situation. For the case in which the threshold value ties at the value $S_2$, i.e. it has previously been raised, for the classification of the scattering behaviour as a fire situation the threshold value $S_2$ may either be left at the value $S_2$ or lowered.

In order to further increase the accuracy of the detection of a fire situation, the scattered radiation fire detector may furthermore have one or more temperature sensors and/or one or more gas sensors. The measurement results of the temperature sensor or sensors, and/or the gas sensor or sensors, may be used in addition to the analysis of the scattered radiation for the decision.

Figure 3:
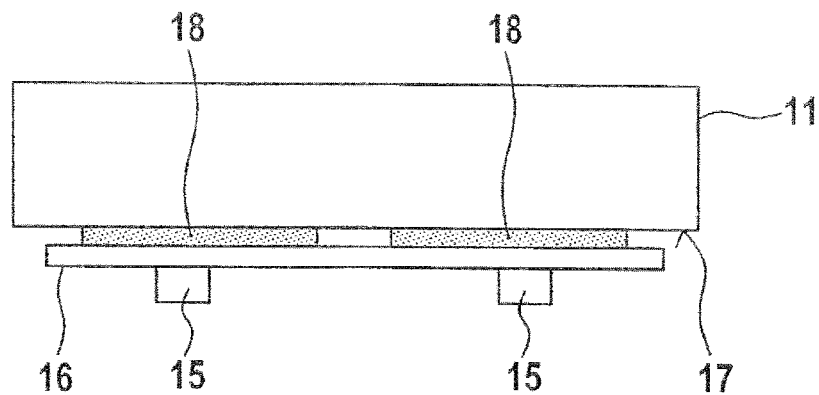
FIG. 3 shows a cross section of a variant of a base body of the scattered radiation fire detector.
Figure 4:
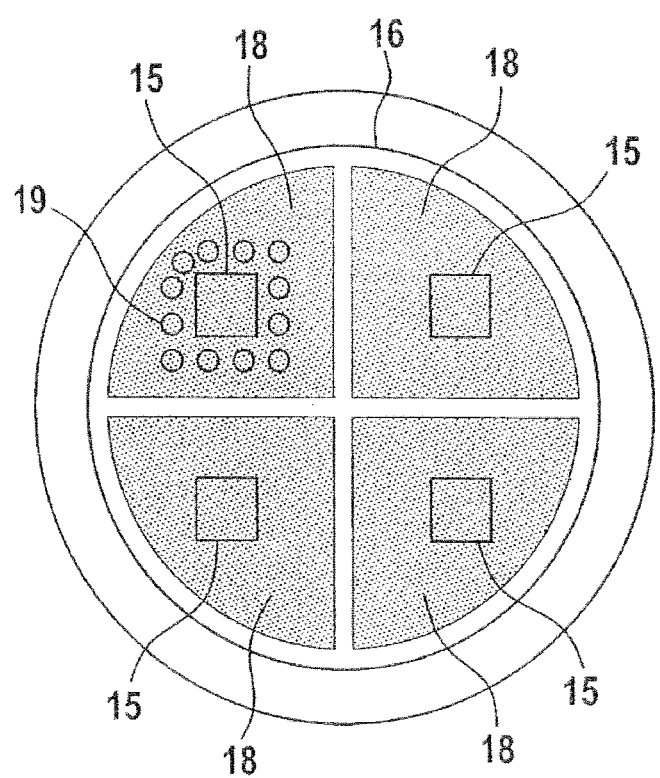
FIG. 4 shows a partially transparent plan view of the base body according to FIG. 3.

FIG. 3 shows a cross section of a variant of a base body 11 of the scattered radiation fire detector, and FIG. 4 shows a partially transparent plan view of the base body according to FIG. 3.

This variant according to FIG. 3 and FIG. 4 differs from the variant previously described and shown in that in addition it also has a heating device. The heating device is formed and provided in order to heat at least the scattering volume.

Heating of the scattering volume may be necessary or expedient in order to avoid moisture condensation situations which, generally speaking, can be causes of erroneous triggering.

In a moisture condensation situation, the fire detector, which is comparatively cold in relation to the environment, is exposed to comparatively warm ambient air of high air humidity. The formation of condensation mist takes place inside the sensor chamber, which may lead to a false alarm.

The effect achieved by the additional heating device is that at least a part of the scattered radiation fire detector can be heated, so that condensation mist and concomitant false alarms can be avoided.

In the present example, the heating device comprises in total four hewing elements 15. The heating elements 15 are, in the present configuration, installed on a circuit board 16. It is to be pointed out that the arrangement and position of the heating elements 15 may also be other than as represented and described.

The circuit board 16 is installed on a lower side 17, facing away from the heating elements 15, of the base body 11, a thermally conductive material 18 which conducts heat to a sufficient extent being arranged between the lower side 17 and the circuit board 16. The thermally conductive material may in particular be a type of paste, a material in paste form, a pad and the like.

The heating elements 15 in the present case are resistive heating elements. For rapid transport of heat by means of convection, bores 19 may additionally be provided in the circuit board 16 and/or the lower side 17 of the base body 11.

In the example shown in FIG. 3 and FIG. 4, the in total four heating elements 15 are installed in a 4-quadrant arrangement. It should be mentioned that other arrangements are also possible and may be implemented. It should furthermore be mentioned that, as regards the number of heating elements 15, there may also be more or fewer heating elements 15. It should also be mentioned that instead of the one circuit board 16, there may also be a plurality of individual circuit boards 16, in which case each circuit board 16 may carry one or more heating elements 15.

In conjunction with an intelligent timer circuit, which may be formed for example as an integrated circuit on the circuit board 16, it is possible to produce different heating powers, for example by means of multistage activation and/or control or regulation of the heating elements 15. In this way, it is possible to react advantageously to a wide variety of temperature situations.

Overall, it can be seen that the objects of the invention are achieved by the proposed scattered radiation fire detector and the corresponding method.

List of References
1 scattered radiation fire detector
2 first radiation source
3 second radiation source
4 scattered radiation sensor
5 scattering volume
6 emission cone
7 reception cone
8 mask
9 principal emission direction
10 principal incidence direction
11 base body
12 first housing
13 second housing
14 further mask
15 heating element
16 circuit board
17 lower side
18 thermally conductive material
19 bore
$\alpha_1, \alpha_2, \alpha_3$: scattering angles

What is claimed is:

1. A scattered radiation fire detector comprising:
two first radiation sources of a first wavelength ($\lambda_1$),
a second radiation source of a longer second wavelength ($\lambda_2$), and
a sensor unit having a scattered radiation sensor sensitive to the first and second wavelengths,
wherein the first radiation sources, the second radiation source and the scattered radiation sensor are arranged and formed in such a way that the optical axes thereof are directed at a common centre of a scattering volume,
wherein forward scattered radiation intensities $I_1(\lambda_{1,fwd})$ of one of the first radiation sources, forward scattered radiation intensities $I_2(\lambda_{2,fwd})$ of the second radiation source and backward scattered radiation intensities $I_3(\lambda_{1,bwd})$ of the other of the first radiation sources are detected by the scattered radiation sensor, and
wherein the sensor unit is configured to calculate the scattered radiation intensity quotients $Q_1=I_1(\lambda_{1,fwd})/I_2(\lambda_{2,fwd})$, $Q_2=I_1(\lambda_{1,fwd})/I_3(\lambda_{1,bwd})$ and $Q_3=I_2(\lambda_{2,fwd})/I_3(\lambda_{1,bwd})$, to detect the existence of a fire situation using the scattered radiation intensity quotients.

2. The scattered radiation fire detector according to claim 1, wherein the first wavelength ($\lambda_1$) lies between 460 nm and 540 nm, and the second wavelength ($\lambda_2$) lies in the infrared spectral range.

3. The scattered radiation fire detector according to claim 2, wherein the first wavelength ($\lambda_1$) lies between 525 nm or at about 470 nm, and the second wavelength ($\lambda_2$) lies between 890 nm and 990 nm.

4. The scattered radiation fire detector according to claim 3, wherein the second wavelength ($\lambda hd 2$) lies at about 940 nm.

5. The scattered radiation fire detector according to claim 1, wherein the first radiation sources, the second radiation source and the scattered radiation sensor are arranged essentially on a circle around the common centre.

6. The scattered radiation fire detector according to claim 1, wherein the scattered radiation sensor is arranged at a forward scattering angle ($\alpha_1, \alpha_3$) of about 60 degrees and at a backward scattering angle ($\alpha_2$) of about 120 degrees, in each case with respect to the principal emission directions.

7. The scattered radiation fire detector according to claim 1, wherein the radiation sources are respectively arranged in first housings which are formed integrally with a base body, and wherein a plurality of barb-shaped fan masks directed transversely to the respective optical axis are arranged between a radiation source and an exit opening of a respective first housing, on both sides of the optical axis of the radiation source, in a symmetrical position relative to the optical axis.

8. The scattered radiation fire detector according to claim 1, wherein the scattered radiation sensor is arranged in a second housing formed integrally with a base body, and wherein a plurality of barb-shaped fan masks directed transversely to the optical axis of the scattered radiation sensor are arranged between the scattered radiation sensor and an entry opening of the second housing, on both sides of the optical axis of the scattered radiation sensor, in a symmetrical position relative to the optical axis.

9. The scattered radiation fire detector according to claim 1, further comprising at least one heating element formed and configured to heat at least the scattering volume, wherein the at least one heating element is arranged outside the scattering volume, on a side, facing away from the scattering volume, of a wall which is adjacent to the scattering volume and bounds the scattering volume.

10. A method for the automatic detection of a fire situation using a scattered radiation fire detector according to claim 1, comprising:
delivering radiation of a first wavelength ($\lambda_1$) into a scattering volume and measuring a first scattered radiation intensity of the first wavelength ($\lambda_1$) generated by forward scattering in the scattering volume;
delivering radiation of the first wavelength ($\lambda_1$) into the scattering volume and measuring a second scattered radiation intensity of the first wavelength ($\lambda_1$) generated by backward scattering in the scattering volume;
delivering radiation of the second wavelength ($\lambda_2$) into the scattering volume and measuring a third scattered radiation intensity of the second wavelength ($\lambda_2$) generated by forward scattering in the scattering volume;
calculating the following first to third scattered radiation intensity quotients $Q_1$, $Q_2$ and $Q_3$:

$$Q_1=I_1(\lambda_{1,fwd})/I_2(\lambda_{2,fwd}), \qquad \text{i)}$$

$$Q_2=I_1(\lambda_{1,fwd})/I_3(\lambda_{1,bwd}), \text{and} \qquad \text{ii)}$$

$$Q_3=I_2(\lambda_{2,fwd})/I_3(\lambda_{1,bwd}); \qquad \text{iii)}$$

classifying the scattering behaviour in the scattering volume with the aid of at least one and/or a combination of several of the scattered radiation intensity quotients; and
making a decision regarding the existence or nonexistence of a fire situation with the aid of the forward scattered radiation intensity $I_2(\lambda_{2,fwd})$ of the second wavelength ($\lambda_2$) and the classification.

11. The method according to claim 10, wherein a forward scattering angle ($\alpha_1, \alpha_3$) is about 60 degrees and the backward scattering angle ($\alpha_2$) is about 120 degrees, in each case with respect to the principal emission directions.

12. The method according to claim 10, wherein the first wavelength lies between 460 and 540 nm, and the second wavelength lies in the infrared spectral range.

13. The method according to claim 12, wherein the first wavelength ($\lambda_1$) lies between 525 nm or at about 470 nm, and the second wavelength ($\lambda_2$) lies between 890 nm and 990 nm.

14. The method according to claim 13, wherein the second wavelength ($\lambda_2$) lies at about 940 nm.

15. The method according to claim 10, wherein the scattering volume is heated by means of a heating element at least while scattered light measurements are being carried out.

* * * * *